United States Patent
Zhu et al.

(10) Patent No.: US 9,999,712 B2
(45) Date of Patent: Jun. 19, 2018

(54) MEDICAL PERISTALTIC PUMP

(71) Applicant: Johnson Electric S.A., Murten (CH)

(72) Inventors: Yue Fu Zhu, Shenzhen (CN);
Mohanlal Ramadoss, Hong Kong (CN)

(73) Assignee: JOHNSON ELECTRIC S.A., Murten (CH)

( * ) Notice: Subject to any disclaimer, the term of this patent is extended or adjusted under 35 U.S.C. 154(b) by 66 days.

(21) Appl. No.: 14/859,890

(22) Filed: Sep. 21, 2015

(65) Prior Publication Data
US 2016/0082168 A1    Mar. 24, 2016

(30) Foreign Application Priority Data

Sep. 19, 2014  (CN) .......................... 2014 1 0484639

(51) Int. Cl.
| | |
|---|---|
| *F04B 43/12* | (2006.01) |
| *A61M 1/10* | (2006.01) |
| *F04B 9/02* | (2006.01) |
| *F04B 9/14* | (2006.01) |
| *F04B 17/03* | (2006.01) |
| *F04B 43/00* | (2006.01) |

(52) U.S. Cl.
CPC ............ *A61M 1/1039* (2014.02); *F04B 9/02* (2013.01); *F04B 9/14* (2013.01); *F04B 17/03* (2013.01); *F04B 43/0072* (2013.01); *F04B 43/0081* (2013.01); *F04B 43/1246* (2013.01); *F04B 43/1261* (2013.01)

(58) Field of Classification Search
CPC .... A61M 1/3621; A61M 1/1037; A61M 1/30; A61M 1/1039
See application file for complete search history.

(56) References Cited

U.S. PATENT DOCUMENTS

| | | | | |
|---|---|---|---|---|
| 3,724,974 A | * | 4/1973 | Molimard | ............... F04B 43/12 417/477.6 |
| 4,142,845 A | * | 3/1979 | Lepp | ................... F04B 43/1276 251/9 |
| 4,558,996 A | * | 12/1985 | Becker | ................ F04B 43/1253 417/374 |
| 4,705,464 A | | 11/1987 | Arimond | |
| 5,549,458 A | * | 8/1996 | Chapman | ............ F04B 43/1253 417/360 |
| 2008/0213113 A1 | * | 9/2008 | Lawrence | ........... A61M 1/1037 417/476 |
| 2011/0208107 A1 | * | 8/2011 | Muller-Spanka | ....... A61M 1/34 604/6.09 |

FOREIGN PATENT DOCUMENTS

JP              62-156178 U     10/1987

* cited by examiner

*Primary Examiner* — Michael D Abreu
(74) *Attorney, Agent, or Firm* — Muncy, Geissler, Olds & Lowe, P.C.

(57) ABSTRACT

A peristaltic pump includes a driver, a pump body, a hose, a rotor and a connecting member. The driver includes a supporting shaft. The pump body includes a chamber housing the rotor. The hose is assembled to an internal side of a wall of the chamber. The connecting member connects the driver with the rotor, and is received in the chamber. The rotor is configured to sequentially squeeze the hose to cause medium in the hose to flow. The connecting member and the rotor rotate about and are supported by the supporting shaft. The medical peristaltic pump has a simple structure and is easy to operate.

14 Claims, 4 Drawing Sheets

MEDICAL PERISTALTIC PUMP

CROSS REFERENCE TO RELATED APPLICATIONS

This non-provisional patent application claims priority under 35 U.S.C. § 119(a) from Patent Application No. 201410484639.1 filed in The People's Republic of China on Sep. 19, 2014, the entire contents of which are hereby incorporated by reference.

FIELD OF THE INVENTION

This invention relates to a medical device and in particular, to a medical peristaltic pump, such as a blood pump.

BACKGROUND OF THE INVENTION

A peristaltic pump, also known as a hose pump, is a type of industrial pump which is used extensively in medical, food, and chemical industries to transport medium which is sensitive, viscous, strongly corrosive, provides grinding effect, has a high purity requirement, or contains a certain amount of granular substances.

A hose is the only essential element of the peristaltic pump for receiving liquid, and a roller or a pressing block squeezes the hose to cause the liquid within the hose to flow. The hose is an independent unit, eliminating the requirement for a hermetically sealed pump body. Therefore, the peristaltic pump is leak-free and very sanitary. In addition, a constant volume of liquid is outputted each time the roller is rotated, enabling the peristaltic pump to provide an outstanding performance in the application of quantifying feed.

However, the structure of the peristaltic pump is complex, with gears of the driver arranged to turn the rotor to which the rollers are fixed, being exposed within the pumping chamber and thus exposing the operator to possible injury when changing the hose.

SUMMARY OF THE INVENTION

There is a desire for a medical peristaltic pump, which has a simplified structure and improved safety, or at least provides the public with a useful choice.

Accordingly, in one aspect thereof, the present invention provides a medical peristaltic pump, comprising: a driver, comprising a supporting shaft; a pump body, comprising a chamber; a rotor received within the chamber; a hose assembled to an internal side of a wall of the chamber; and a connecting member connecting the driver with the rotor, and being received in the chamber; wherein the rotor is configured to sequentially squeeze the hose to cause medium in the hose to flow, the supporting shaft supports the connecting member and the rotor, and the connecting member and the rotor are arranged to rotate about the supporting shaft.

Preferably, the rotor is detachably mounted to the connecting member.

Preferably, the connecting member comprises a plurality of latching claws, the rotor comprises a plurality of locking members, each latching claw is provided with a barb/a latching cutout, each locking member is provided with a latching cutout/a barb to latch with the corresponding barb/latching cutout.

Preferably, the rotor comprises a main body, the main body defines a receiving groove for the latching claw, the main body defines a guiding groove, the locking member being slidable within the guiding groove, a resilient member is provided between the locking member and the main body, the resilient member pushes the locking member to maintain the locking member in a position which allows the latching cutout/barb of the locking member to latch with the corresponding barb/latching cutout.

Preferably, the connecting member is provided with at least one step to position the rotor axially relative to the chamber.

Preferably, the rotor comprises a main body, a sliding block capable of sliding relative to the main body, a roller assembled to a terminal end of the block, and a spring arranged to move the sliding block radially outwardly to urge the roller into contact with the hose.

Preferably, the main body comprises at least one positioning surface, the sliding block defines at least one abutting surface, the abutting surface of the sliding block engages with the corresponding positioning surface of the main body, thereby positioning the sliding block.

Preferably, the pump body further comprises a cover configured to cover the chamber, the cover is connected to the chamber by a hinge.

Preferably, the pump body further comprises a cover for covering the chamber, and an electromagnetic locking mechanism is provided between the cover and the chamber.

Preferably, one of the cover and the chamber is equipped with a permanent magnet, the other one is equipped with a sensor, and the sensor interacts with the magnet to sense an open or close state of the cover.

Preferably, the driver comprises an electric motor and a gear reduction mechanism, the gear reduction mechanism comprises an output gear, the output gear is disposed outside the chamber and fixedly connected to the connecting member.

Preferably, the rotor comprises a cover plate, and the cover plate has a handle for manual rotation of the rotor.

BRIEF DESCRIPTION OF THE DRAWINGS

A preferred embodiment of the invention will now be described, by way of example only, with reference to figures of the accompanying drawings. In the figures, identical structures, elements or parts that appear in more than one figure are generally labeled with a same reference numeral in all the figures in which they appear. Dimensions of components and features shown in the figures are generally chosen for convenience and clarity of presentation and are not necessarily shown to scale. The figures are listed below.

DETAILED DESCRIPTION OF THE PREFERRED EMBODIMENTS

Figure 1:
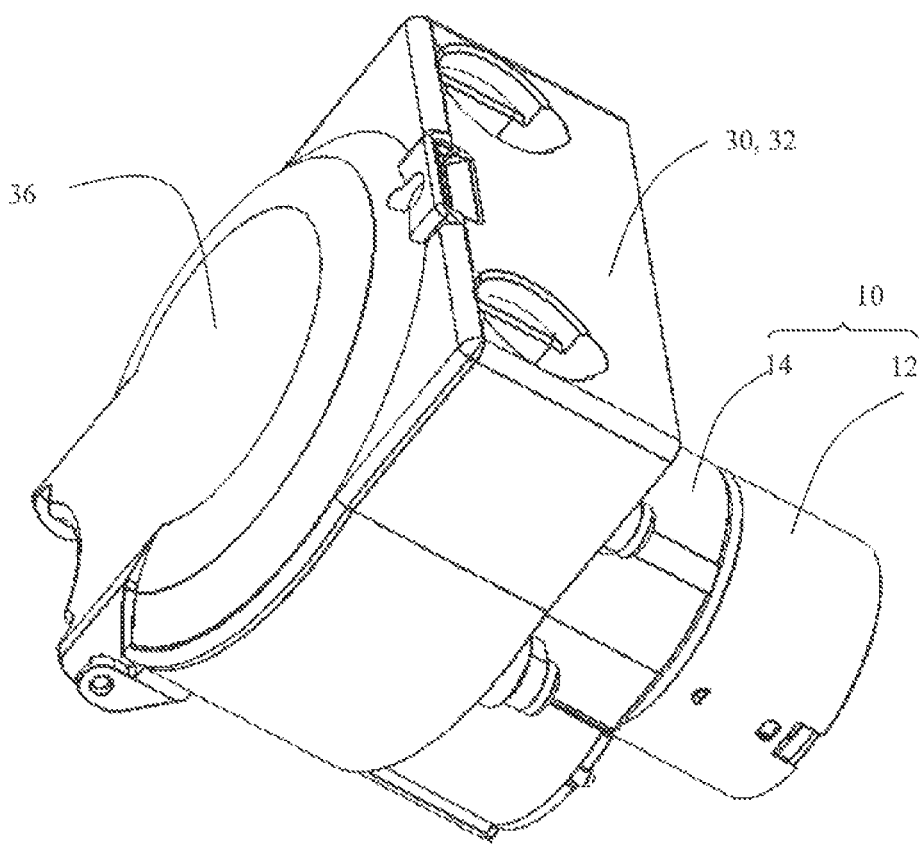
FIG. 1 illustrates a medical peristaltic pump in accordance with an embodiment of the invention.
Figure 2:
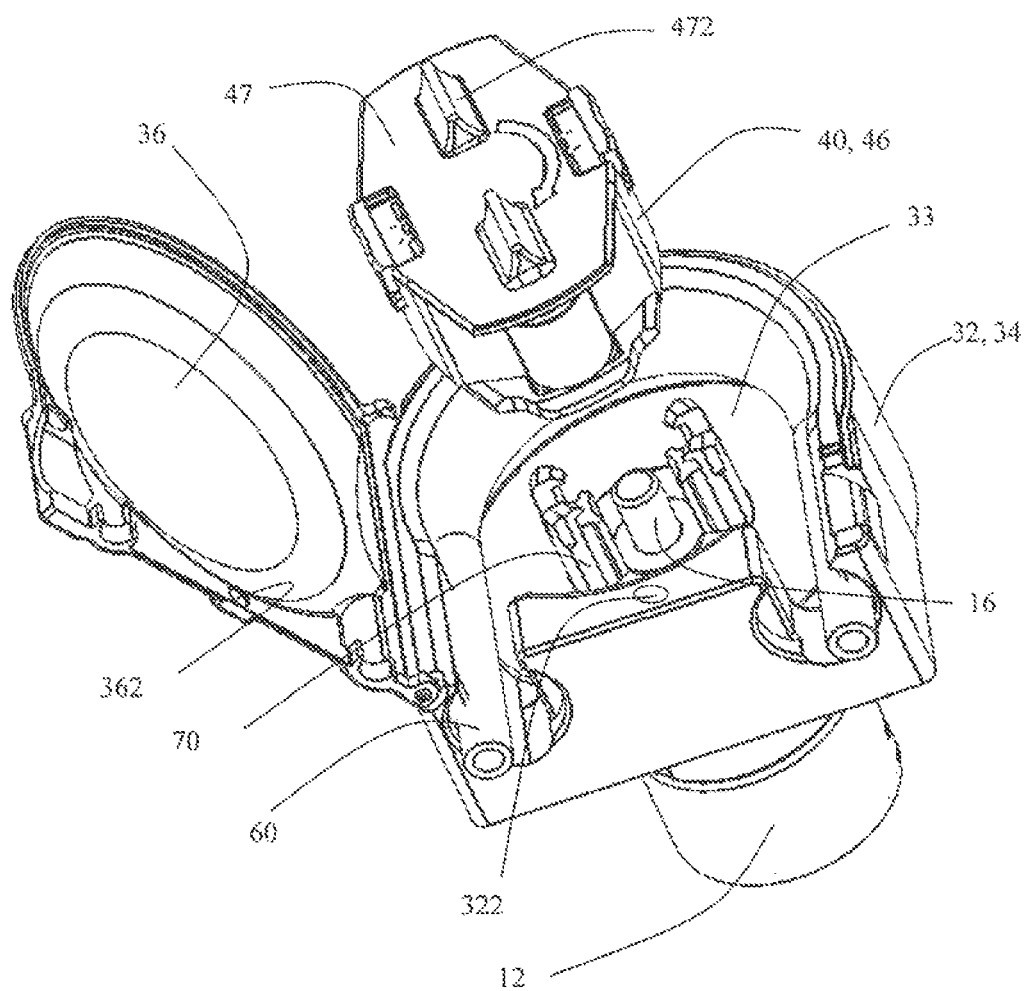
FIG. 2 is a partially exploded view of the medical peristaltic pump of FIG. 1, with a cover opened.

Referring to FIGS. 1 and 2, a medical peristaltic pump in accordance with an embodiment of the invention includes a driver 10, a pump body 30 and a hose 60.

The driver 10 includes an electric motor 12, and a gear reduction mechanism 14 driven by the electric motor 12.

The pump body 30 includes a chamber 32, and a rotor 40 received in the chamber 32. The rotor 40 is configured to squeeze the hose 60, so as to cause the (liquid) medium, such as blood, within the hose 60 to flow. The chamber 32 includes an arc wall 34, and a portion of the hose 60 closely contacts an internal surface of the arc wall 34. The internal surface of the arc wall 34 is a portion of a cylindrical surface. A center of the internal surface coincides with a center of the rotor 40.

Figure 3:
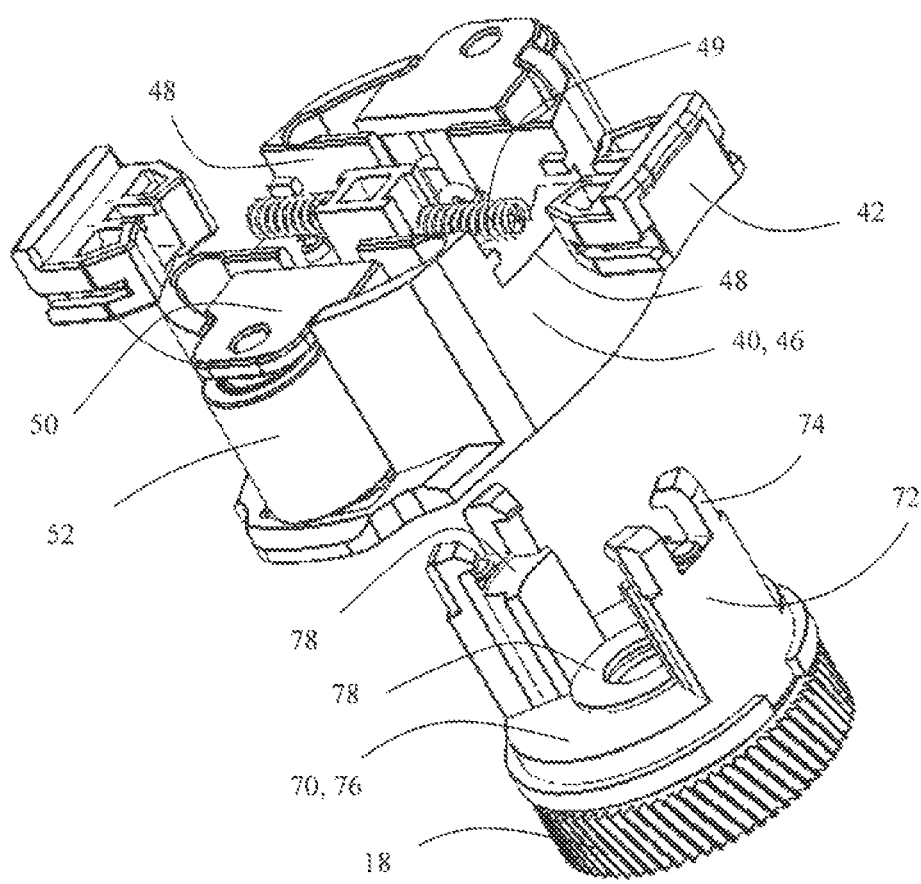
FIG. 3 is an exploded view of a rotor and a connecting member of the medical peristaltic pump of FIG. 1.

The gear reduction mechanism 14 includes a supporting shaft 16 and an output gear 18 (see FIG. 3). A connecting member 70 is fixedly connected to the output gear 18. The supporting shaft 16 extends through the output gear 18 and the connecting member 70, thereby allowing the output gear 18 and the connecting member 70 to rotate about the supporting shaft 16. The connecting member 70 is received in the chamber 32, the rotor 40 is detachably connected to the connecting member 70, thereby the rotor 40 can be fixed to rotate with the output gear 18 via the connecting member 70. The output gear 18 is shielded at a side of a bottom plate 33 of the chamber 32 remote from the rotor 40, i.e. the output gear 18 is disposed outside of the chamber 32, such that the output gear 18 is protected and the user is prevented from being hurt by the output gear 18.

Figure 4:
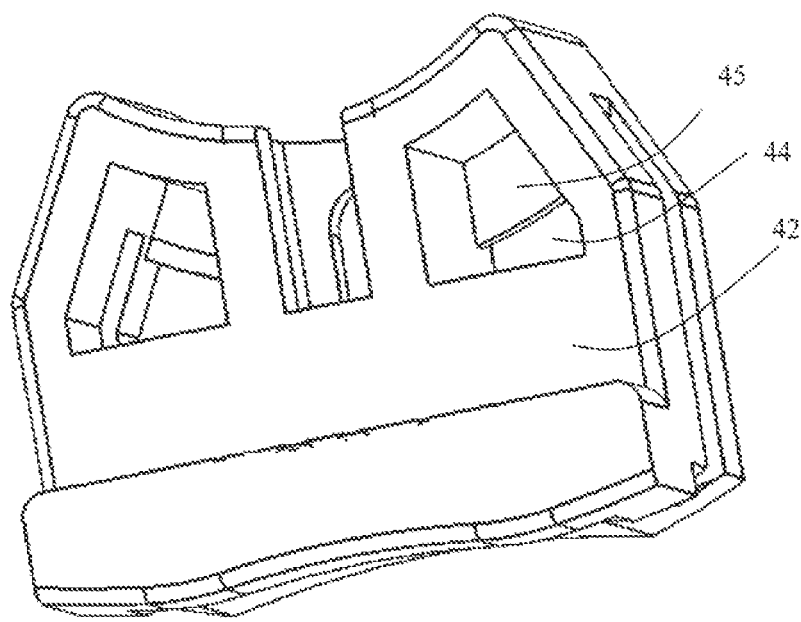
FIG. 4 shows a locking member of the rotor of FIG. 3.
Figure 6:
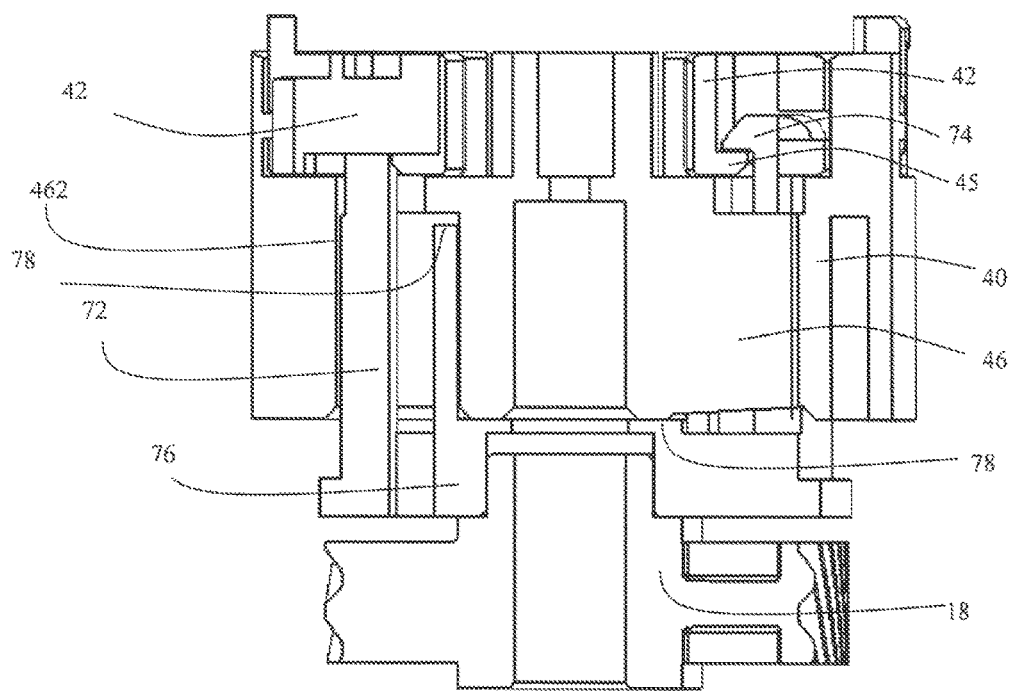
FIG. 6 is a sectional view of the rotor of FIG. 5.

Referring to FIG. 3 and FIG. 4, the connecting member 70 includes a plurality of latching claws 72 latching with the rotor 40. Each latching claw 72 is provided with a barb 74 at a terminal end thereof. The rotor 40 includes a plurality of locking members 42, and each locking member 42 defines a latching cutout 44 for latching with the barb 74. The rotor 40 further includes a main body 46. The main body 46 defines a groove 462 (FIG. 6) extending in an axial direction of the main body 46, for insertion of the latching claw 72. The main body 46 defines a guiding groove 48 at a portion corresponding to the locking member 42. The locking member 42 can slide within the guiding groove 48. A resilient member such as a spring 49 is disposed between the locking member 42 and the main body 46 in a resiliently compressed condition. The spring 49 urges the locking member 42 to remain in a position that enables the barb 74 of the connecting member 70 to latch with the latching cutout 44 of the locking member 42.

Specifically, the locking member 42 defines two latching cutouts 44, and a bottom of an end of each latching cutout 44 adjacent to the spring 49 is provided with a blocking plate 45 extending from a side wall of the latching cutout 44 toward the latching cutout 44. On application of an external force, the locking member 42 is moved against the force of the spring 49 and slides inwardly relative to the main body 46, enabling the blocking plate 45 in the latching cutout 44 to move away from the barb 74, allowing the latching claw to enter the latching cutout 44. Once the barb 74 clears the blocking plate 45, the spring returns the latching member to the locked position capturing the latching claws contact between the blocking plate and the barb. Under the urgings of the spring 49, the locking member 42 comes back to an original position, the barb 74 of the connecting member 72 resists against the block plate 45 of the latching cutout 44, thereby securing the connecting member 70 to the rotor 40 to enable the rotor 40 to rotate together with the connecting member 70. In the illustrated embodiment, the spring 49 is positioned between a central portion of the main body 46 and an internal end portion of the locking member 42. The spring 49 pushes the locking member 42 outward. The barb 74 of the connecting member 70 resists an internal side wall of the latching cutout 44, i.e. the barb 74 contacts the side wall nearest to the center of the main body 46, to prevent the locking member 42 which is under the urging of the spring 49 from sliding outward excessively and disengaging from the rotor main body. Depressing the latching member against the urging of the spring releases the latching claws allowing the rotor to be disconnected for the connecting member.

Preferably, the connecting member 70 includes two latching claws 72, and each latching claw 72 is provided with a pair of barbs 74 at an end portion thereof. Each locking member 42 defines a pair of latching cutouts 44, and each pair of the barbs 74 is positioned within a corresponding latching cutout 44. Such arrangement can strengthen a connection between the connecting member 70 and the rotor 40.

The connecting member 70 further includes a connecting portion 76. Preferably, the connecting portion 76 is annular in shape, with a though hole defined in a center thereof. The output gear 18 of the driver 10 is fixedly assembled to the end of the connecting portion 76 remote from the latching claw 72. The supporting shaft 16 extends though the output gear 18 and the connecting portion 76, thereby rotatably supporting the output gear 18 and the connecting member 70.

The connecting member 70 is provided with at least one step to position an axial portion of the rotor 40 in the chamber 32. In the embodiment, an end of the connecting portion 76 of the connecting member 70 adjacent to the latching claw 72 is provided with a protruded step 78 at a center thereof. The latching claw 72 is also provided with a step 78 at a position adjacent to the barb 74, the step 78 abuts against the main body 46 of the rotor 40 (see FIG. 6). The engagement between the barb 74 and the step 78 can define the axial position of the rotor 40 relative to the connecting member 70.

Figure 5:
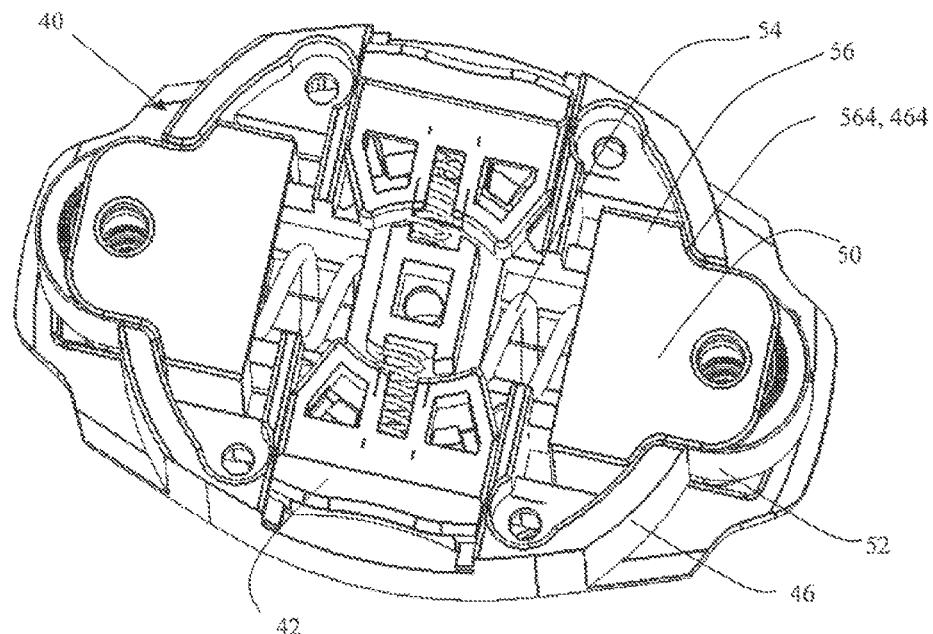
FIG. 5 shows the rotor of the medical peristaltic pump of FIG. 1, with a rotor cover removed to show an internal structure of the rotor.

Referring to FIG. 5, the rotor 40 further includes a plurality of sliding blocks 50 which can slide relative to the main body 46, a plurality of rolling posts or rollers 52 assembled to a terminal end of the sliding block 50, which can rotate relative to sliding block 50, and a spring 54 positioned between the central portion of the main body 46 and the internal end of the sliding block 50. The spring 54 urges the sliding block 50 outwardly to enable the roller 52 to squeeze the hose 60. Specifically, the main body 46 defines a receiving space receiving the sliding blocks 50, the sliding blocks 50 can slide within the receiving space. The sliding block 50 is provided with a shoulder portion 56, and the main body 46 defines an arc positioning surface 464 corresponding to the shoulder portion 56 of the sliding block 50. The shoulder portion 56 defines an abutting surface 564 configured to contact the positioning surface 464, and the abutting surface 564 has a shape corresponding to the shape of the positioning surface 464 of the main body 46. The positioning surface 464 engages with the shoulder portion 56 of the sliding block 50 to limit a maximum distance of movement of the sliding block 50, thereby controlling the utmost position of the roller 52. Preferably, the plurality of arc positioning surfaces 464 of the main body 46 are located on a coaxial circle having a center on the axis of the rotor. The center of the coaxial circle is on the axis of the supporting shaft 16, i.e. the center of the rotor 40. This facilitates keeping a concentricity of the plurality of the sliding blocks 50, i.e. keeping the distances uniform between the utmost edges of the rollers 52 on the plurality of the sliding blocks 50 and the center of the rotor 40, thereby maintaining the same squeezing force of the rollers 52 of different sliding blocks 50 on the hose to achieve the constant medium flow.

Referring to FIG. 2, the hose 60 is arranged in a substantially U shape, and assembled to the inner side of the side portion of the chamber 32. In operation, the output gear 18 of the driver 10 drives the rotor 40 to rotate via the connecting member 70, and the rollers 52 on the rotor 40 squeeze the hose 60 along the extending direction of the hose 60, thereby pushing the medium in the hose 60 to move along the hose in the direction of rotation of the rotor 40.

The rotor 40 further includes a cover plate 47. The cover plate 47 is fixed to the main body 46 via a fixing member such as a screw. A side of the cover plate 47 remote from the main body 46 is provided with a handle 472, such that when the driver 10 stops working, the user can use the handle 472 to turn the rotor 40.

The pump body 30 further includes a cover 36 configured to cover the chamber 32. The cover 36 is connected to the chamber 32 by a hinged connection.

Preferably, an electromagnetic lock is provided between the cover 36 and the chamber 32. A permanent magnet 362 is fixed to one of the cover 36 and the chamber 32, and a sensor 322 such as a Hall sensor is assembled to the other one. When the cover 36 is closed, the sensor 322 generates a signal to indicate that the cover 36 is closed. When the cover 36 is open, the sensor 322 generates another signal to indicate that the cover 36 is open.

The medical peristaltic pump of the invention is specially suitable for use as a blood pump. When serving as a blood pump, the rotating rate of the output gear 18 is preferably 80-120 revolutions/minute (RPM).

In the description and claims of the present application, each of the verbs "comprise", "include", "contain" and "have", and variations thereof, are used in an inclusive sense, to specify the presence of the stated item or feature but do not preclude the presence of additional items or features.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of example only, and various other modifications will be apparent to persons skilled in the field without departing from the scope of the invention as defined by the appended claims.

For example, the locking member and the connecting member can be connected in different detachable connecting manners. When the engagement between a latching hook and a latching cutout is adopted, the positions of the latching hook and the latching cutout are not intended to be limited to any particular positions described above. The latching hook can be positioned on one of the locking member and the connecting member, and the latching cutout can be positioned on the other one. It can also adopt an engagement between a latching hook and a latching clip. These all fall within the scope of the invention. Therefore, the scope of the invention is to be determined by reference to the claims that follow.

The invention claimed is:

1. A medical peristaltic pump, comprising:
 a driver, comprising a supporting shaft;
 a pump body, comprising a chamber;
 a rotor received within the chamber;
 a hose assembled to an internal side of a wall of the chamber; and
 a connecting member connecting the driver with the rotor, and being received in the chamber;
 wherein the rotor is configured to sequentially squeeze the hose to cause medium in the hose to flow, the supporting shaft supports the connecting member and the rotor, and the connecting member and the rotor are arranged to rotate about the supporting shaft, and wherein the rotor is detachably mounted to the connecting member, the connecting member comprises a plurality of latching claws, the rotor comprises a plurality of locking members, each latching claw is provided with a barb/a latching cutout, each locking member is provided with a latching cutout/a barb to latch with the corresponding barb/latching cutout, the rotor comprises a main body, the main body defines a receiving groove for the latching claw, the main body defines a guiding groove, the locking member being slidable within the guiding groove, a resilient member is provided between the locking member and the main body, the resilient member pushes the locking member to maintain the locking member in a position which allows the latching cutout/barb of the locking member to latch with the corresponding barb/latching cutout.

2. The pump of claim 1, wherein the rotor comprises a sliding block capable of sliding relative to the main body, a roller assembled to a terminal end of the block, and a spring arranged to move the sliding block radially outwardly to urge the roller into contact with the hose.

3. The pump of claim 2, wherein the main body comprises at least one positioning surface, the sliding block defines at least one abutting surface, the abutting surface of the sliding block engages with the corresponding positioning surface of the main body, thereby positioning the sliding block.

4. The pump of claim 1, wherein the pump body further comprises a cover for covering the chamber, and an electromagnetic locking mechanism is provided between the cover and the chamber.

5. The pump of claim 4, wherein one of the cover and the chamber is equipped with a permanent magnet, the other one is equipped with a sensor, and the sensor interacts with the magnet to sense an open or close state of the cover.

6. The pump of claim 1, wherein the connecting member is provided with at least one step to position the rotor axially relative to the chamber.

7. The pump of claim 1, wherein the pump body further comprises a cover configured to cover the chamber, the cover is connected to the chamber by a hinge.

8. The pump of claim 1, wherein the driver comprises an electric motor and a gear reduction mechanism, the gear reduction mechanism comprises an output gear, the output gear is disposed outside the chamber and fixedly connected to the connecting member.

9. The pump of claim 1, wherein the rotor comprises a cover plate, and the cover plate has a handle for manual rotation of the rotor.

10. A medical peristaltic pump, comprising:
 a driver comprising a supporting shaft;
 a pump body comprising a chamber;
 a rotor received within the chamber;
 a hose assembled to an internal side of a wall of the chamber; and
 a connecting member connecting the driver with the rotor, and being received in the chamber;

wherein the rotor is configured to sequentially squeeze the hose to cause medium in the hose to flow, the connecting member and the rotor are driven by the driver to rotate about the supporting shaft, the rotor comprises a main body and at least two locking members slidably coupled to the main body, the connecting member comprises at least two latching claws to latch the corresponding locking members, and a resilient member is provided between the main body and each locking member to push the locking member to latch with the corresponding latching claw.

11. The pump of claim 10, wherein the rotor comprises a sliding block capable of sliding relative to the main body, a roller assembled to a terminal end of the block, and a spring arranged to move the sliding block radially outwardly to urge the roller into contact with the hose.

12. The pump of claim 11, wherein the main body comprises at least one positioning surface, the sliding block defines at least one abutting surface, the abutting surface of the sliding block engages with the corresponding positioning surface of the main body, thereby positioning the sliding block.

13. The pump of claim 10, wherein the connecting member is provided with at least one step to position the rotor axially relative to the chamber.

14. The pump of claim 10, wherein the driver comprises an electric motor and a gear reduction mechanism, the gear reduction mechanism comprises an output gear, the output gear is disposed outside the chamber and fixedly connected to the connecting member.

* * * * *